United States Patent
Tolentino et al.

Patent Number: 5,523,446
Date of Patent: Jun. 4, 1996

[54] PROCESS FOR PREPARING A MIXTURE OF ALKOXYACYLOXY SILANE AND ALKYLTRIACYLOXSILANE

[75] Inventors: Luisito A. Tolentino, Clifton Park; Lewis O. Slocum, Mecanicville; Russell L. Wilt, Clifton Park, all of N.Y.

[73] Assignee: General Electric Company, Waterford, N.Y.

[21] Appl. No.: 538,687

[22] Filed: Oct. 3, 1995

[51] Int. Cl.$^6$ .................................................. C07F 7/02
[52] U.S. Cl. .................................................. 556/442
[58] Field of Search .................................................. 556/442

[56] References Cited

U.S. PATENT DOCUMENTS

| | | |
|---|---|---|
| 4,176,130 | 11/1979 | John et al. |
| 4,298,753 | 11/1981 | Schinabeck et al. |
| 4,329,484 | 11/1981 | Petersen. |
| 4,332,956 | 1/1982 | Tolentino .................... 556/442 |
| 4,410,677 | 10/1983 | Lampe. |
| 5,187,291 | 2/1993 | Seiler et al. .................... 556/442 |
| 5,387,706 | 2/1995 | Rasmussen et al. .................... 556/442 |

*Primary Examiner*—Paul F. Shaver

[57] ABSTRACT

A continuous method is provided for making a mixture of alkylpolyacyloxysilane and alkoxyacyloxysilane which is useful as a curing catalyst for a one part moisture curable silicone RTV. A steady-state mixture of alkylpolyacyloxysilane and alkoxyacyloxysilane is established in the reboiler of a distillation system having a reboiler, a distillation column, and a condenser as a result of the continuous introduction into the distillation column of a mixture of an alkyltrichlorosilane and silicon tetrachloride and the direct feeding of an alcohol such as tertiary butanol into the reboiler. A mixture comprising alkylpolyacyloxysilane and alkoxyacyloxysilane and aliphatic carboxylic is continuously pumped to a collection vessel. The continuous stripping and recycling of the aliphatic carboxylic from the collection vessel results in the continuous production of the desired silane mixture.

5 Claims, No Drawings

PROCESS FOR PREPARING A MIXTURE OF ALKOXYACYLOXY SILANE AND ALKYLTRIACYLOXSILANE

BACKGROUND OF THE INVENTION

The present invention relates to a continuous process for making an acyloxysilane mixture having up to about 40 percent by weight of alkoxyacyloxysilane, such as di-tertiarybutoxydiacetoxy silane. More particularly, the present invention relates to a method of initially feeding into a distillation column, a mixture of an alkyltrichlorosilane, such as methyltrichlorosilane, silicon tetrachloride, and an aliphatic carboxylic acid, such as acetic acid; concurrently, an alcohol, such as tertiary -butanol is separately introduced into the reboiler; a mixture of polyacyloxysilane and alkoxyacyloxysilane is continuously recovered from the reboiler in a separate receiving vessel. Acyloxy silanes are commonly used as cross-linking agents for one-part silicone RTV compositions. A procedure for making an acyloxysilane such as methyl triacetoxysilane is by reacting a chlorosilane such as methyltrichlorosilane with acetic anhydride. However, this procedure results in the formation of acetyl chloride which is a hazardous material.

Mixtures of acyloxysilane and alkoxyacyloxysilane also have been used as cross-linking agents for low modulus silicone RTV compositions, as shown by Lampe, U.S. Pat. No. 4,410,677. A continuous process for making alkoxysilanes and alkoxysiloxanes is shown by Schinabeck et al, U.S. Pat. No. 4,298,753. Methods for preparing acyloxysilanes by reacting chlorosilanes and aliphatic carboxylic acids are shown by John et al U.S. Pat. No. 4,176,130 and Petersen U.S. Pat. No. 4,329,484. Additional procedures for making mixtures of polyacyloxysilane and alkoxyacyloxysilane are therefor constantly being evaluated.

SUMMARY OF THE INVENTION

The present invention is based on the discovery that mixtures of polyacyloxysilane and alkoxyacyloxysilane can be made in a continuous manner by separately introducing into a reboiler containing a steady-state mixture of a polyacyloxysilane and alkoxyacyloxysilane, an alcohol and the product of reaction of a mixture of an alkyltrichlorosilane, silicon tetrachloride and an aliphatic carboxylic acid, such as acetic acid. Experience has shown, that HCl, which is generated in the reaction, can be recovered as a by-product, if desired. A typical reaction involving the aforesaid reactants in forming the mixtures of polyacyloxysilane and alkoxyacyloxysilane is as follows:

$CH_3SiCl_3 + SiCl_4 + $ excess $CH_3CO_2H$

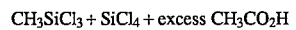

$CH_3Si(OCOCH_3)_3 + Si(OCOCH_3)_4 + 7HCl$

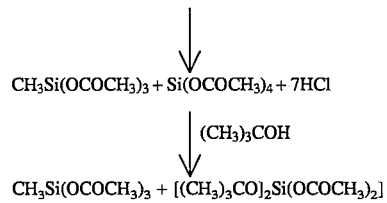

$CH_3Si(OCOCH_3)_3 + [(CH_3)_3CO]_2Si(OCOCH_3)_2]$

Experience has shown that prior to the introduction of the alkyltrichlorosilane, silicon tetrachloride and an aliphatic carboxylic acid, optimum results are achieved if a mixture of the polyacyloxysilane and alkoxyacyloxysilane is initially continuously charged to the reboiler, along with excess aliphatic carboxylic acid, such as acetic acid to produce a mixture which achieves a steady-state condition. The mixture is heated until reflux of the aliphatic carboxylic acid is observed. It has been found that a steady- state mixture is achieved if the mixture has about 60 to about 80% by weight of the polyacyloxysilane, and about 15 to about 40 weight of the alkoxyacyloxysilane based on the weight of mixture.

STATEMENT OF THE INVENTION

There is provided by the present invention, a continuous method for making a mixture useful as a curing catalyst for a one-part moisture curable silicone RTV composition, which method comprises, (1) continuously forming a steady-state mixture in the reboiler of a distillation system comprising a reboiler, a distillation column, and a condenser, where the steady- state mixture comprises, an aliphatic carboxylic acid, and a silane mixture comprising about 60 to about 80% by weight of alkylpolyacyloxysilane, and about 15 to about 40 weight of alkoxyacyloxysilane, based on the weight of silane mixture, (2) continuously introducing into the reboiler while the steady-state mixture is refluxing, (a) a $C_{(1-8)}$ alcohol, and (b) reactants originating from the distillation column comprising a mixture of alkyl trichlorosilane and silicon tetrachloride and an aliphatic carboxylic acid, (3) continuously venting from the condenser, hydrogen chloride formed from the mixture of (2), (4) continuously recovering from the reboiler, a mixture comprising alkylpolyacyloxysilane, alkoxyacyloxysilane and aliphatic carboxylic acid, (4) continuously distilling the aliphatic carboxylic acid from the mixture of (4) and continuously returning it to the distillation column, and (5) continuously recovering a mixture comprising alkylpolyacyloxysilane and alkoxyacyloxysilane from the mixture of (4).

Alcohols which can be used in the practice of the present invention are for example tertiary butyl alcohol, which is preferred. Additional alcohols which can be used are for example, methyl alcohol, ethyl alcohol, propyl alcohol, isopropyl alcohol, butyl alcohol and other $C_{(1-8)}$ alcohols.

$C_{(1-8)}$ alkyl trichlorosilanes which can be used in the practice of the invention are for example, methyltrichlorosilane. Other alky trichlorosilanes which can be used are for example, ethyl trichlorosilane, propyl trichlorosilane, isopropyl trichlorosilane, butyl trichlorosilane, isobutyl trichlorosilane and other $C_{(1-8)}$ alkyl trichlorosilanes.

It is preferred to employ acetic acid as the aliphatic carboxylic acid in the practice of the invention. However, additional aliphatic carboxylic acids, such as formic, propionic, butyric, valeric, and dimethyl acetic also so can be used.

In the practice of the preferred form of the invention, a mixture of alkylchlorosilane and silicon tetrachloride is continuously fed into the upper half of a distillation column which is connected below to a reboiler. A condenser is positioned above the distillation column. A steady-state mixture providing refluxing aliphatic carboxylic acid, and a mixture of polyacyloxysilane and alkoxyacyloxysilane is continuously maintained in the reboiler. Alcohol, such as tertiary butanol is continuously fed directly into the reboiler. A mixture of alkypolyacyloxy silane, alkoxyacyloxysilane, such as dialkoxydiacyloxysilane and aliphatic carboxylic acid is continuously pumped from the bottom of the reboiler to a product collection vessel. The mixture of alkypolyacyloxy silane and alkoxyacyloxysilane is continuously recovered as a bottoms product while the aliphatic carboxylic acid is continuously stripped therefrom; the aliphatic carboxylic acid is continuously passed through a heater and recycled to the upper half of the distillation column and preferably above the feed point of the alkylchlorosilane and silicon tetrachloride mixture. Hydrogen chloride is continuously collected as it exits from the condenser positioned above the distillation column.

A preferred procedure for forming the steady-state mixture is to initially charge a mixture of the polyacyloxysilane and alkoxyacyloxysilane to the reboiler within the proportions as previously stated in the Statement of the Invention.

The mixture of polyacyloxysilane and alkoxyacyloxysilane which is continuously formed in the practice of the present invention, can be used as a catalyst and as an adhesion promoter in moisture curable silicone RTV compositions.

The following examples are given by way of illustration and not by way of limitation. All parts are by weight unless otherwise specified.

EXAMPLE 1

There was charged into the reboiler of a distillation system consisting of a reboiler, a 36 inch×1 inch jacketed column attached vertically above thereto, and a condenser attached to the top of the column, 150 g of a mixture of 50% by weight of acetic acid, 32.5% by weight of methyltriacetoxysilane (MTAS), and 17.5% by weight of ditertiarybutyldiacetoxysilane (DTBDACS). The reboiler mixture was heated to reflux.

A silane blend of 65% by weight of methyltrichlorosilane and 35% by weight of silicon tetrachloride was fed into the jacketed column at room temperature at a rate of 1 ml/per minute. Acetic acid preheated at 100°–115° C. was introduced at a rate of 3.30 ml/minute ( 102% excess based on reactive SiCl) into the column at a point above the silane blend. Tertiary butanol was fed into the reboiler at 0.5 ml/min (2 moles/mole of silicon tetrachloride). The reboiler contents were held to a constant volume by using a pump which delivered the reaction product to a 1 liter product collection vessel. A steady state column temperature of 94°–110° C. was established while the reboiler temperature was 125°–127° C. HCl gas was vented to a water acid scrubber. At the end of a 7½ hour run, 2138 g of product was recovered in the collection vessel. The product was stripped at 100°–101° C. at 15 torr to provide 777 g of product. The stripped product was analyzed by gas chromatography; it showed the following:

| Composition | % Area |
| --- | --- |
| acetic acid | 1.7 |
| methyltriacetoxysilane (MTAS) | 54.0 |
| di-tertiarybutoxydiacetoxysilane (DTBDACS) | 23.4 |
| dimethyltetraacetoxysilane ('dimer') | 3.8 |
| di-tertiarybutoxydiacetoxysilane ('dimer') | 2.4 |
| high boilers | 14.7 |

The above results show that the major product is a mixture of the MTAS and the DTBDACS within the scope of the present invention. This composition can be used as a curing catalyst and as an adhesion promoter for a moisture curable silicone RTV:

EXAMPLE 2

The procedure of example 1 was repeated, except that 150 g of a solution containing 50% by weight of acetic acid, 33.3% by weight of of MTAS, and 16.7% by weight of DTBDACS were charged to the reboiler and heated to reflux. A silane blend of 66.7% by weight of methyltrichlorosilane, and 33.3% by eight of silicon tetrachloride was fed at into the jacketed column at a 1 ml/minute rate. Preheated acetic acid was fed into the column at a point above the silane mixture at a 3.5 ml/min (115 mole % excess) rate. The contents of the reboiler were held to a constant volume using a pump and maintained at a temperature of 80°–85° C. Tertiary butanol was charged to the reboiler at a 0.4 ml/min rate (2 moles of butanol/mole of silicon tetrachloride). Steady-state mixture was formed in two hours while maintaining a temperature of 70°–114° C. and 124°–139° C. across the column and the reboiler respectively. There was obtained 1214 g of stripped product after a 12 hour run. The stripped product showed the following after after gas chromatograpic analysis:

| Composition | % Area |
| --- | --- |
| acetic acid | 2.3 |
| MTAS | 60.4 |
| DTBDACS | 14.4 |
| MTAS dimer | 4.4 |
| DTBDACS dimer | 2.6 |
| high boilers | 15.9 |

The above mixture also containing a major proportion of MTAS and DTBDACS is useful as a curing catalyst for a silicone RTV composition.

EXAMPLE 3

In accordance with the procedure of example 2, 150 g of a mixture containing 50% by weight of acetic acid, 36.3% by weight of MTAS, and 13.7% of DTBDACS was charged to the reboiler. A silane blend containing 72.7% by weight of methyltrichlorosilane and 27.3% by weight of silicon tetrachloride was fed into the column at a rate of 1 ml/min (119 mole % excess). After a 12 hour run, there was obtained 925 g of stripped product. Based on gas chromatographic analysis, the product had the following composition:

| Composition | % Area |
| --- | --- |
| acetic acid | 0.8 |
| MTAS | 68.5 |
| DTBDACS | 15.8 |
| MTAS dimer | 3.2 |
| DTBDACS | 2.0 |
| high boilers | 9.7 |

The above composition is useful as a curing catalyst for a moisture curable silicone RTV composition.

What is claimed is:

1. A continuous method for making a mixture useful as a curing catalyst for a one-part moisture curable silicone RTV composition, which method comprises, (1) forming a steady-state mixture in the reboiler of a distillation system comprising a reboiler, a distillation column, and a condenser, where the steady- state mixture comprises, an aliphatic carboxylic acid, and a silane mixture comprising about 60 to about 80% by weight of alkylpolyacyloxysilane, and about 15 to about 40 weight of alkoxyacyloxysilane, based on the weight of silane mixture, (2) introducing into the reboiler while the steady-state mixture is refluxing, (a) a $C_{(1-8)}$ alcohol, and (b)

reactants originating from the distillation column comprising a mixture of a $C_{(1-8)}$ alkyltrichlorosilane and silicon tetrachloride and an aliphatic carboxylic acid, (3) venting from the condenser, hydrogen chloride formed from the mixture of (2), (4) recovering from the reboiler, a mixture comprising alkylpolyacyloxysilane, alkoxyacyloxysilane and aliphatic carboxylic acid, (4) distilling the aliphatic carboxylic acid from the mixture of (4) and continuously returning it to the distillation column, and (5) recovering a mixture comprising alkylpolyacyloxysilane and alkoxyacyloxysilane from the mixture of (4).

2. A continuous method in accordance with claim 1, where the aliphatic carboxylic acid is acetic acid, the $C_{(1-8)}$ alkyltrichlorosilane is methyl trichlorosilane, and the $C_{(1-8)}$ alcohol is di-tertiary butanol.

3. A continuous method in accordance with claim 1, where the mixture comprising alkylpolyacyloxysilane, alkoxyacyloxysilane and aliphatic carboxylic acid is continuously pumped from the reboiler to a collection vessel while the aliphatic carboxylic acid is continuously stripped therefrom.

4. A continuous method in accordance with claim 3, where the aliphatic carboxylic acid is continuously passed through a heater and fed back to the distillation column.

5. A continuous method in accordance with claim 1, where hydrogen chloride is vented from the condenser.

* * * * *

UNITED STATES PATENT AND TRADEMARK OFFICE
CERTIFICATE OF CORRECTION

PATENT NO. : 5,523,446

DATED : June 4, 1996

INVENTOR(S) : Luisito A. Tolentino, Lewis O. Slocum, Russell L. Wilt

It is certified that error appears in the above-indentified patent and that said Letters Patent is hereby corrected as shown below:

At Column 2, line 31, (4) should be (5) and at Column 2, line 34, (5) should be (6)

At Column 5, line 9, (4) should be (5) and at Column 5 Line 12, (5) should be (6)

Signed and Sealed this

Twenty-ninth Day of October 1996

Attest:

BRUCE LEHMAN

Attesting Officer                Commissioner of Patents and Trademarks